United States Patent [19]

Fry et al.

[11] Patent Number: 4,805,628
[45] Date of Patent: Feb. 21, 1989

[54] ULTRASOUND CONTRAST MEDIA FOR MEDICALLY IMPLANTABLE AND INSERTABLE DEVICES

[75] Inventors: Francis J. Fry; Burney, Bryan T., both of Indianapolis, Ind.

[73] Assignee: Indianapolis Center For Advanced Research, Inc., Indianapolis, Ind.

[21] Appl. No.: 447,262

[22] Filed: Dec. 6, 1982

[51] Int. Cl.$^4$ .............................................. A61B 10/00
[52] U.S. Cl. ................................................ 128/662.02
[58] Field of Search .................................. 128/660–663

[56] References Cited

U.S. PATENT DOCUMENTS

| 3,640,271 | 2/1972 | Horton . | |
|---|---|---|---|
| 4,122,713 | 10/1978 | Stasz et al. . | |
| 4,265,251 | 5/1981 | Tickner | 128/662 X |
| 4,265,252 | 5/1981 | Chuffuch et al. | 128/748 |
| 4,276,885 | 7/1981 | Tickner et al. . | |
| 4,316,271 | 2/1982 | Evert | 128/660 X |
| 4,349,033 | 9/1982 | Eden | 128/660 |

FOREIGN PATENT DOCUMENTS

| 2509584 | 7/1976 | Fed. Rep. of Germany | 128/663 |
|---|---|---|---|
| 2911354 | 2/1980 | Fed. Rep. of Germany | 128/660 |

OTHER PUBLICATIONS

Madsen, E.L. et al., "An Anthropomorplic Torso Section Phantom for UTS Imaging", Med. Phys. 7(1), Jan.-/Feb. 1980.

*Ultrasonics In Clinical Diagnosis*, edited by P. N. T. Wells (Second Edition).
J. Maroon, J. Edmonds-Seal & R. Campbell, "An Ultrasonic Method For Detecting Air Embolism", J. Neurosurgery, vol. 31 (Aug. 1969).
M. Resnick & W. Boyce, "Ultrasonography of the Urinary Bladder, Seminal Vesicles and Prostate", Chapter 12 in Ultrasound in Urology by Resnick & Sanders (1979).
W. Fairbank, Jr. & M. Scully, "A New Noninvasive Technique for Cardiac Pressure Measurement: Resonant Scattering of Ultrasound from Bubbles", IEEE Transactions on Biomedical Engineering (Mar. 1977).
P. Colley & R. Martin, "Intravascular Doppler Catheter For Detection of Air Emboli", Anesthologists Annular Meeting (1978).
R. Nishi, "Ultrasonic Detection of Bubbles With Doppler Flow Transducers".

*Primary Examiner*—Francis J. Jaworski
*Attorney, Agent, or Firm*—Barnes & Thornburg

[57] ABSTRACT

A method is provided for enhancing ultrasound detection of implantable or insertable devices which can be placed in bodies. The method includes the steps of providing a space in the device having a substantially gas-impermeable wall, and filling the space with a gas. A medically implantable or insertable device having an enhanced ultrasound detectability is also provided. The device includes a substantially gas-impermeable portion which defines a space. The space is filled with a gas or mixture of gases to enhance ultrasound detection, and determination of the location of the device.

3 Claims, 1 Drawing Sheet

U.S. Patent      Feb. 21, 1989      4,805,628
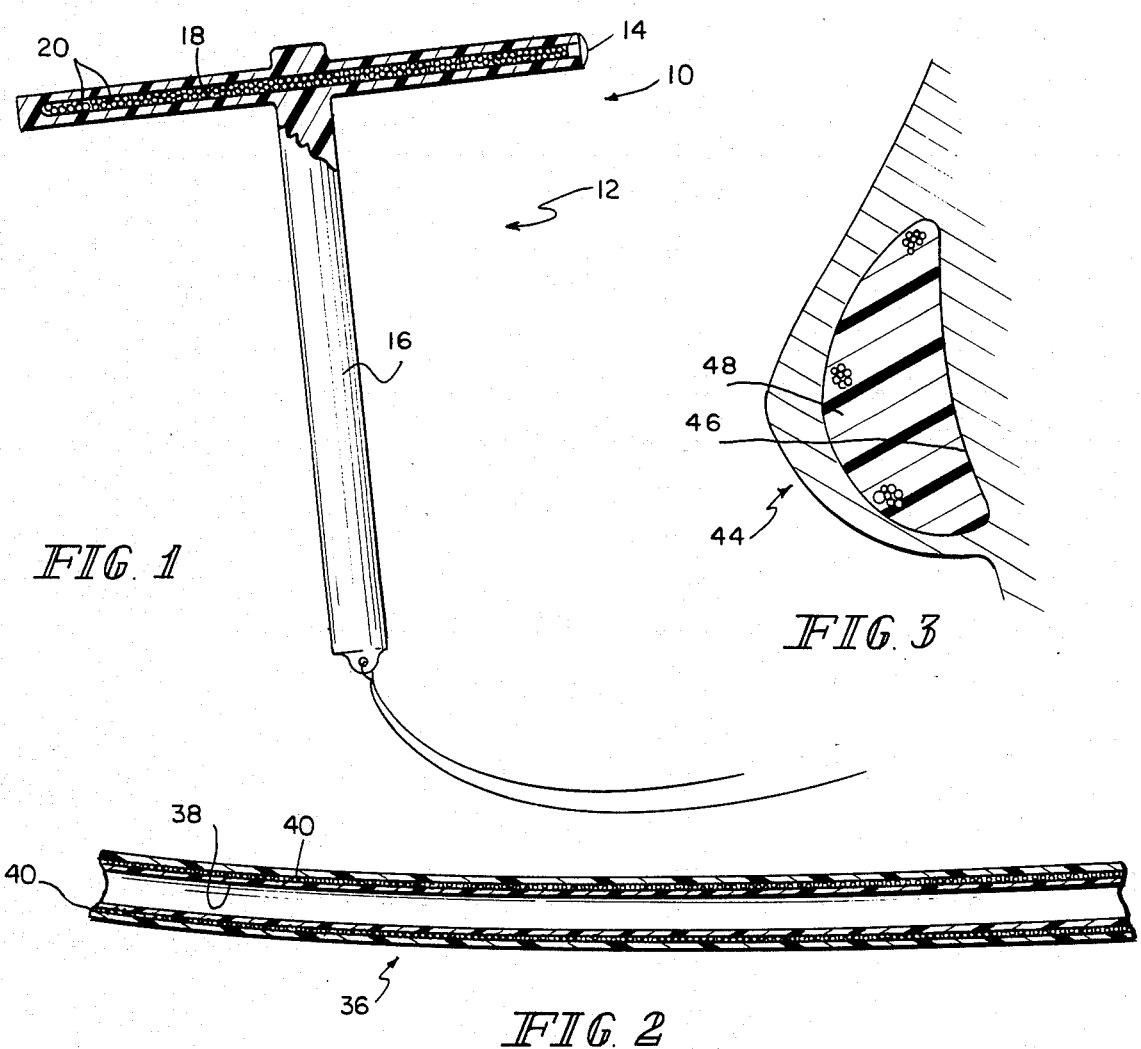
FIG. 1
FIG. 3
FIG. 2
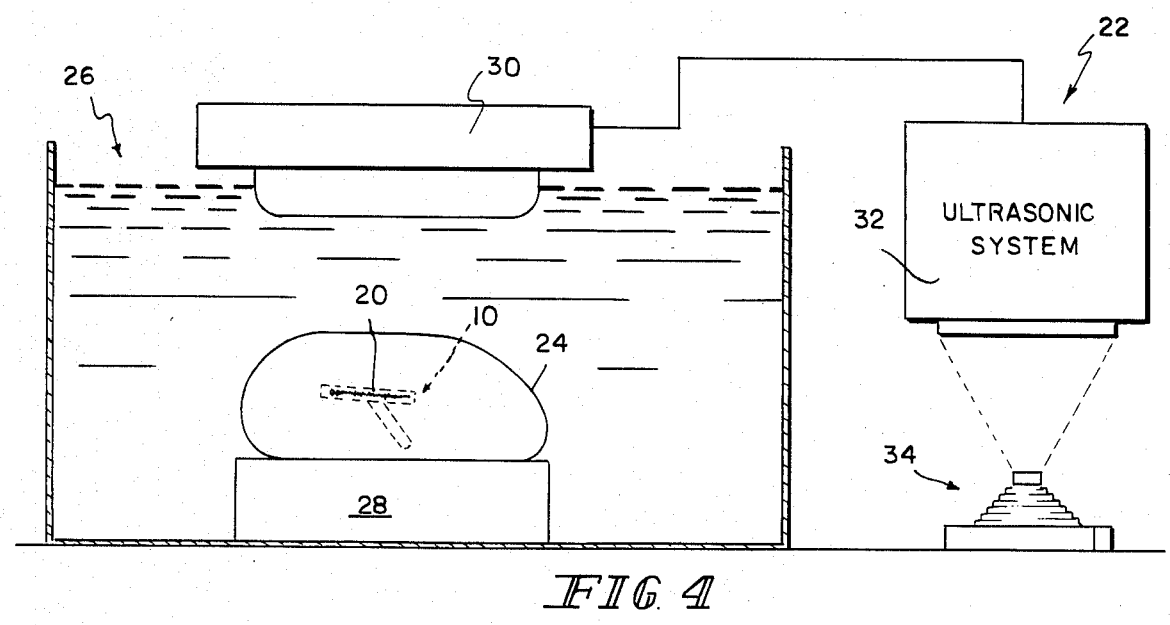
FIG. 4

ULTRASOUND CONTRAST MEDIA FOR MEDICALLY IMPLANTABLE AND INSERTABLE DEVICES

BACKGROUND OF THE INVENTION

This invention relates to medically implantable or insertable devices, and more particularly to devices which are designed to be detectable by ultrasound, and methods for enhancing ultrasound detection of these devices.

Medical science has devised a number of devices for long-term implantation or insertion into the human body. Some of these devices are prosthetic devices designed to replace natural parts of the body which malfunction. Common examples of such devices are false teeth, artifical hips, and synthetic blood vessels and heat valves. Other devices are implanted or inserted in the body to perform functions other than replacing existing natural parts. Common examples of such devices are pacemakers to regulate heart beat and intrauterine devices to prevent pregnancy.

Intrauterine devices are objects, foreign to the body, which are inserted inside the uterus to prevent pregnancy. The mechanisms through which they act are not completely understood by medical science. It is believed that intrauterine devices (IUDs) have been known since antiquity, finding their origin in the placement of stones in the uteri of camels to prevent pregnancies during long caravan journeys. Modern IUDs had their origin around the turn of the century with the introduction of the Richter silkworm gut IUD. During the 1920's and 30's, the Grafenberg ring and Ota ring were developed. Some examples of currently used IUDs include the Lippes Loop, the Saf-T-Coil, the Copper 7, the Copper T, and the Progestasert. The above-mentioned IUDs are of different shapes and different sizes. Generally, they are constructed of polyethylene or some other biocompatible plastic. The Copper 7 and the Copper T IUDs include a fine copper wire which enhances the contraceptive properties of the IUD. The Progestasert IUD includes progesterone which is selectively released into the uterus to both enhance the infertility-inducing properties of the IUD, and to reduce the undesirable complications caused by the IUD. Several IUDs are impregnated with barium or titanium dioxide to increase the radiopacity of the IUD, and thus make them visible on radiographs.

Most IUDs now include transcervical nylon tails, which monitor the correct placement of the IUD and facilitate its removal. Generally, the nylon tail extends partially into the vagina to enable the user to manually inspect for the presence of the IUD.

Several undesirable complications have been associated with the use of IUDs. Among these are infection, bleeding, uterine perforation, cervical laceration, septic abortion, ectopic pregnancy, and expulsion of the IUD by the user. Expulsion is undesirable in that if the IUD is expelled, it can no longer provide protection against pregnancy. For many of the above-mentioned complications, the examining physician must be able to detect the positioning and placement of the IUD in order to diagnose the problem, and to prevent further complications.

Perhaps the most common side effect of IUDs is abnormal bleeding, taking the form of either menorrhagia, metrorrhagia, or both. A disparity between the size and shape of the uterine cavity and the IUD and inaccurate (non-fundal) placement of the device at the time of insertion have both been linked to IUD-induced increases in uterine bleeding.

Another potentially very serious complication of IUDs is that of perforation. Uterine perforation is the penetration of the IUD through the wall of the uterine corpus. Cervical perforation is the penetraton of the IUD through the uterine cervix. Uterine perforations can be either complete or partial perforations. Complete perforations are those perforations wherein the IUD has completely passed through the uterine wall. Partial perforations are those wherein part of the IUD is still within the uterus or myometrium. Perforations can be either primary or secondary. Primary perforations are those perforations which occur at the time the IUD is inserted into the user. Secondary perforations are those which occur after the IUD has been inserted. It is important for the examining physician to be able to detect the presence and location of IUDs in the user. Extrauterine IUDs have been reported to have caused intestinal obstructions and bowel obstructions resulting in serious complications. Further, deaths have been reported from amniotic fluid embolism following spontaneous abortion in the second trimester in association with uterine perforation.

Currently, there are several techniques for determining the presence and position of IUDs in the uterus. One technique involves the use of X-rays. Many IUDs are treated with various materials to be radiopaque. There are serious difficulties, however, associated with the use of X-ray detection. X-rays are believed to be capable of inducing chromosomal abnormalities in the ova contained in the ovaries. Because of the close spatial relation between the uterus and the ovaries, it is generally wise to reduce the use of X-rays in this area whenever possible.

Another detection technique involves the use of sounds. Sounds are instruments which are introduced into the body to detect foreign matter. Physicians also will often examine the marker strings which are attached to the IUD to detect the presence and position of the IUD. Another technique is to manipulate the uterus under fluorscopic examination. In some cases, a second IUD has been inserted into the uterus to serve as an intra-uterine marker to detect relative placement of the lost IUD. Also, various ultrasound techniques have been used to locate the IUD in the uterus.

SUMMARY OF THE INVENTION

In accordance with the instant invention, a medically implantable or insertable device is provided which comprise a substantially gas-impermeable portion which defines a space. The space is filled with a gas or mixture of gases to enhance ultrasound detection and determination of the location of the device.

Also according to the instant invention, a method is provided for enhancing the ultrasonic detection of implantable or insertable devices which are placed in the body. The method comprises the steps of providing a space in the device which has a substantially gas-impermeable wall. The space is filled with a gas or a mixture of gases.

One feature of the instant invention is that a device which is inserted or implanted for long-term residence in the body is made more visible to ultrasound. This feature has the advantage of enabling health care personnel to detect more easily the positioning of the device, thereby facilitating the detection of both problems in placement of the device and problems with the device itself. This feature is especially advantageous with devices such as IUDs where placement of the device is important to the proper functioning of the device, and the avoidance of harmful complications to the user.

Another advantage of this feature is that the positioning of the device can be ascertained without a physical intrusion into the area of the body wherein the device is implanted or inserted. Further, the position can be ascertained without resorting to the use of potentially hazardous radiation sources such as X-ray. This advantage is especially important in applications such as IUDs, which are positioned near reproductive cells.

Additional features and advantages of the invention will become apparent to those skilled in the art upon consideration of the following detailed description of a preferred embodiment exemplifying the best mode of carrying out the invention as presently perceived.

BRIEF DESCRIPTION OF THE INVENTION

The detailed description particularly refers to the accompanying figures in which:

FIG. 1 is a cross-sectional view of an intrauterine device employing the instant invention;

FIG. 2 is a cross-sectional view of an artificial blood vessel employing the instant invention;

FIG. 3 is a vertical sectional view, in situ, of a breast prosthesis employing the instant invention; and FIG. 4 is a diagrammatic illustration of the testing apparatus employed with this invention.

DETAILED DESCRIPTION

Devices for long-term insertion, such as intrauterine devices, and devices for implantation, such as breast prostheses, heart valves, and blood vessels are fabricated from materials which are idealized from a biocompatibility standpoint. Examples of such materials include plastics, such as polyethylene and ethylene/vinyl acetate copolymers. Although the materials are well-suited for construction of such devices from a standpoint of biocompatibility, the devices made of these materials are often difficult to detect or visualize with ultrasound diagnostic instrumentation. Medical implantable devices often have X-ray dense materials embedded in the devices to aid in the detection of the devices with ionizing radiation. Ultrasound detection, however, requires a different approach using gaseous inclusions in order to maximize accoustic impedance or bulk modulus differences in the device. For some devices, a sheet-type gaseous inclusion will optimize specular reflection. In other devices, a number of small gas bubble inclusions will optimize scattering in an omnidirectional manner. These methods alone, or in combination, can be used to optimize the ultrasound detection of medically implantable or inertable devices.

A medically insertable device 10 shown in FIG. 1 such as a Progestasert intrauterine progesterone contraceptive system 12 manufactured by Alza Corporation, Palo Alto, Calif., includes a base member 14 and a stem member 16. The IUD 12 is constructed of an ethylene/vinyl acetate copolymer containing titanium dioxide. It also includes barium sulfate or radiopacity. Base member 14 includes a fluid-filled portion 18 which is normally filled with a fluid such as silicone. To make the IUD 12 more visible to ultrasound, some of the silicone contained in the fluid-filled portion 18 is drained and replaced with gas represented by bubbles 20. The material of the base member 14 surrounding the fluid-filled portion 18 is preferably comprised of a gas-impermeable material to retard the flow of gas bubbles 20 out of the fluid-filled portion 18.

The detectability of a Progestasert IUD 12 by ultrasound was tested in the testing apparatus 22 diagrammatically illustrated in FIG. 4. The in vitro test involved a formalin fixed human uterus 24 suspended in a water bath medium 26. The uterus 24 was placed upon base 28 which was aligned with a 5 MHz linear phased array transducer system 30 which was operatively connected to an ultrasound system 32. Ultrasound system 32 was operatively connected to a Polaroid camera 34 to photograph that which the ultrasound system 32 and transducer 30 detected.

In testing for ultrasound detectability, a conventional IUD, without gas inclusions, was observed in test apparatus 22 with ultrasound and its detectability was quantified.

Some of the fluid contained in fluid-filled portion 18 was removed from a similar Progestasert IUD 12, and gas bubbles 20 were inserted therein. The bubbles 20 were inserted in a quantity sufficient to retain the original size and shape of the fluid-filled (non gas-containing) IUD. When the gas included IUD 12 was viewed with ultrasound, the detectability of the IUD 12 immediately increased on the order of 6 to 10 dB.

The small size of the Progestasert IUD 12 makes it difficult to modify the IUD 12 to give a specular reflection at diagnostic ultrasound frequencies from gaseous medium insertion. The Progestasert IUD is, however, well-suited to the introduction of gas, or a mixture of gases, in bubble form 20, to produce high levels of back scattered ultrasound.

When an IUD not having a gas inclusion was detected with the ultrasound, the IUD was barely detectable, even with the gain settings of the ultrasound system 32 at its maximum level. When an IUD 12, having gas inclusions such as bubbles 20, was detected, the IUD 12 was clearly detectable, and its position within the uterus 24 clearly ascertainable, even with the gain setting greatly reduced.

The uterus 24 is also visible to ultrasound by reconciling the position of the IUD 12 with the position of the uterus 24. In reconciling the relative positions of the uterus 24 and IUD 12, the examining health care personnel can determine whether the IUD 12 is properly placed within the uterus 24. The medical personnel will be able to determine whether the IUD 12 has perforated the uterus 24 or cervix (not shown). If the IUD 12 has partially or fully perforated the uterus 24 or cervix, the physician, by knowing the position of the IUD, is better able to plan an appropriate strategy for removal of the IUD 12. The gas inclusions will enable the IUD 12 to be detectable by ultrasound even in many cases wherein the IUD 12 is in an extrauterine position.

An implantable device made according to the instant invention is a synthetic blood vessel section 36 having an inner liner 38 through which blood flows and an outer liner 40 surrounding inner liner 38. Preferably, both inner liner 38 and outer liner 40 are constructed of a gas-impermeable material. Inner liner 38 and outer liner 40 define a space 42 between the inner 38 and outer 40 liners into which a gas can be inserted. Due to the impermeability of inner liner 38 and outer liner 40, gas will be retained in space 42 permanently. Gas may be inserted into space 40 either in the form of bubbles or in the form of a sheet. By forming space 42 to retain gas in sheet-like disposition, specular reflection will be optimized.

A breast prosthesis 44 is shown in FIG. 3. Generally, a breast prosthesis includes a sack-like wall 46 which is filled with a silicone fluid. A gas, or a mixture of gases, illustrated as bubbles 47, is inserted into the silicone-containing portion 48 of the prosthesis 44 in order to enable the physician to detect the placement and positioning of the prosthesis 44 by ultrasound.

Although the invention has been described in detail with reference to certain preferred embodiments and specific examples, variations and modifications exist within the scope and spirit of the invention as described and as defined in the following claims.

What is claimed is:

1. A method for enhancing ultrasound detection of an implantable or insertable device which can be placed in a body comprising the steps of providing a space in the device having a substantially gas-impermeable wall, and placing a sheet-like inclusion of gas within the space.

2. An ultrasonically detectable device for relatively permanent or long-term insertion or implantation into a body comprising means for defining a space for receiving and substantially permanently retaining a gas in the form of a plurality of gaseous bubbles, and a plurality of gaseous bubbles inserted into the space.

3. An ultrasonically detectable device for relatively permanent or long-term insertion or implantation into a body comprising means for defining a space for receiving and substantially permanently retaining a gas in the form of a sheet, and a gas in the form of a sheet inserted into the space.

* * * * *